(12) United States Patent
Del Soldato et al.

(10) Patent No.: US 7,776,902 B2
(45) Date of Patent: Aug. 17, 2010

(54) NITROOXYDERIVATIVES OF CYCLOOXYGENASE-2 INHIBITORS

(75) Inventors: Piero Del Soldato, Monza (IT); Giancarlo Santus, Milan (IT)

(73) Assignee: Nicox S.A., Sophia Antipolis (FR)

( * ) Notice: Subject to any disclaimer, the term of this patent is extended or adjusted under 35 U.S.C. 154(b) by 1373 days.

(21) Appl. No.: 10/516,938

(22) PCT Filed: Jun. 20, 2003
(Under 37 CFR 1.47)

(86) PCT No.: PCT/EP03/06502

§ 371 (c)(1),
(2), (4) Date: Sep. 13, 2005

(87) PCT Pub. No.: WO04/000781

PCT Pub. Date: Dec. 31, 2003

(65) Prior Publication Data

US 2006/0106082 A1    May 18, 2006

(30) Foreign Application Priority Data

Jun. 25, 2002    (IT) .......................... MI2002A1391

(51) Int. Cl.
*A61K 31/415*    (2006.01)
*C07D 231/10*    (2006.01)
(52) U.S. Cl. .................................. 514/406; 548/377.1
(58) Field of Classification Search .................. 514/406; 548/377.1
See application file for complete search history.

(56) References Cited

U.S. PATENT DOCUMENTS 5,994,381 A    11/1999    Haruta et al.

FOREIGN PATENT DOCUMENTS

| EP | 0 722 434 B1 | 4/1995 |
| EP | 0 759 899 B1 | 11/1995 |
| WO | WO 96/13483 A | 5/1996 |
| WO | WO 96/25405 A | 8/1996 |
| WO | WO 98 09948 A | 3/1998 |
| WO | WO 99/11605 A | 11/1999 |
| WO | 00/51988 A1 | 9/2000 |
| WO | 00/61537 A2 | 10/2000 |
| WO | 00/61541 A2 | 10/2000 |
| WO | WO 01 45703 A | 6/2001 |
| WO | WO 02/30866 | 4/2002 |

OTHER PUBLICATIONS

Mamidi et al., Pharmacological and Pharmacokinetic Evaluation of Celecoxib Prodrugs in Rats, 2002, Biopharmaceutics and Drug Disposition, 23, p. 275.*
J.R. Vane et al., "Cyclooxygenases 1 and 2", *Annu. Rev. Pharmacol. Toxicol.* 38, 97-120, 1998.
A. Lichtenstein et al., "Effects of Different Forms of Dietary Hydrogenated Fats on Serum Lipoprotein Cholesterol Levels", *N. Engl. J. Med.* 340(25), 1933-2005, 1999.
D. Riendeau et al., "Etoricoxib (MK-0663): Preclinical Profile and Comparison with Other Agents That Selectively Inhibit Cyclooxygenase-2", *J. Pharmacol. Exp. Ther.* 296(2), 558-566, 2001.
M.N. Muscará et al., "Vasorelaxant effects of a nitric oxide-releasing aspirin derivative in normotensive and hypertensive rats", *Br. J. Pharmacl.* 133, 1314-1322, 2001.

* cited by examiner

*Primary Examiner*—Kamal A Saeed
*Assistant Examiner*—Kristin Bianchi
(74) *Attorney, Agent, or Firm*—Arent Fox LLP

(57) ABSTRACT

New compounds able to release COX-2 inhibitors and NO having formula (I):

$$M\text{-}T\text{-}Y_A\text{---}NO_2 \qquad (I)$$

for the treatment and/or prophylaxis of inflammatory processes.

13 Claims, No Drawings

NITROOXYDERIVATIVES OF CYCLOOXYGENASE-2 INHIBITORS

CROSS-REFERENCE TO RELATED APPLICATION

This application is a National Stage entry of International Application No. PCT/EP03/006502 filed Jun. 20, 2003, the entire specification and claims of which are incorporated herewith by reference.

The present invention relates to nitro-derivatives of cyclooxygenase-2 inhibitors (thereafter referred to as COX-2 inhibitors), pharmaceutical compositions containing them and their use for the treatment and/or prophylaxis of inflammations, such as for example arthritis, osteoarthritis, rheumatoid arthritis, dysmenorrhea, pain and fever, gastrointestinal and cardiovascular disorders, rheumatic diseases, neoplasia and Alzheimer's disease, for mitigating or removing the known side-effects of COX-2 inhibitors and for treating and/or preventing disorders resulting from elevated levels of cyclooxygenase-2.

Cyclooxygenase is the enzyme that converts arachidonic acid into prostanoids. Further to the development of non-steroidal anti-inflammatory drugs (NSAIDs), it became easily clear that for said compounds there is a strict and direct relationship between activity and toxicity. In fact, even though they inhibit the cyclooxigenase activity, preventing the formation of pro-algogen/inflammatory prostanoids, on the other hand they give rise to a reduction of protective prostanoids, so that injury to the gastrointestinal tract is the obvious result. Further studies have demonstrated that there are two different types of cyclooxygenase enzymes: the so called constitutive form (COX-1), responsible for the production of the protective prostanoids, and the inducible form (COX-2), producing the pro-algogen/inflammatory prostanoids (J. R. Vane et al., Ann. Rev. Pharmacol. Toxicol. 1998, 38:97-120). Therefore, it has been postulated that the NSAIDs anti-inflammatory effects are mediated by COX-2 inhibition, whereas their side effects are due to the inhibition of COX-1. However, it is known that COX-1 enzyme is physiologically concerned with the generation of prostaglandins exhibiting a protective effect on gastric mucous membrane, at renal and gastrointestinal level as well as on the platelets aggregation. Hence anti-inflammatory drugs specifically inhibiting COX-2 without inhibition of COX-1 should be free from the side effects associated with conventional NSAID. It has been then verified that to a patient taking a selective COX-2 inhibitor also a NSAID should be administered for having cardioprotective action; however, in this way he will not be free from gastrointestinal inconveniences. In the same way, switching from a non-steroidal anti-inflammatory drug to a selective COX-2 inhibitor, the cardioprotective activity will be lost, gaining however in anti-arthritic properties. On the ground of these concepts, selective COX-2 inhibitors have been developed having the desired therapeutic profile of an anti-inflammatory drug without the adverse effects commonly associated with the inhibition of COX-1. However, all these compounds have demonstrated to not be free from side effects, as for example dyspepsia and gastropathy, as well as gastrointestinal and cardiovascular risks (Mohammed et al., N. Engl. J. Med., 340(25)2005, 1999). Notwithstanding the continuous development of always new COX-2 inhibitors, the problem of their side effects is still unresolved. So is has been reported about the potential risk of cardiovascular events, acute colitis, gastrointestinal haemorrhage, allergic vasculitis, intestinal diseases.

In WO 01/45703 nitrosated and nitrosylated cyclooxygenase-2 inhibitors as well as compositions comprising at least one of these new inhibitors, and, optionally, at least one compound that donates, transfers or releases nitric oxide are described. In said application it is stated that the adverse effects of the known COX-2 inhibitors can be diminished or prevented if said inhibitors contain at least a nitrite, nitrate, thionitrite or thionitrate group. In particular, in this patent were exemplified the preparations of compounds containing the —O—$NO_2$ group (nitrosated cyclooxygenase-2 inhibitors) directly linked to the COX-2 inhibitor moiety and the synthesis of COX-2 inhibitors derivatives containing the —S—NO group (nitrosylated cyclooxygenase-2 inhibitors) indirectly linked to the precursor drugs. inhibitors.

It was an object of the present invention to provide new derivatives of cyclooxygenase-2 inhibitors not having the disadvantages mentioned above and that are transformed in vivo in compounds with enhanced COX-2 inhibiting activity and that release molecules able to modulate the bioavailability of nitrogen oxide so as to reduce or resolve the problems at cardiovascular and/or gastrointestinal level and to obtain a synergic action between COX-2 molecule and nitric oxide.

Object of the present invention are compounds or salts thereof with enhanced pharmacological profile which are able to release COX-2 inhibitors and NO (nitrogen oxide) under conditions and according to the parameters set up in test 1 described below, having the general formula (I)

$$M\text{-}T\text{-}Y_A\text{—}NO_2 \qquad (I)$$

wherein

M-T is the residue of a COX-2 selective inhibitor, in which T=—$SO_2NH$—, —$SO_2NR$—, —(CO)—, —O—, —S—, —NH—, —N($SO_2R$)—, R being alkyl with 1-10 carbon atoms, preferably methyl, wherein the COX-2 selective inhibitor, M-TH or M-TOH, has to meet test 2 described below;

$Y_A$=—$(B)_{b0}$—$(C)_{c0}$— wherein:

b0 e c0 are the integers 1 or 0, with the proviso that b0 and c0 cannot be simultaneously 0, B=-$T_B$-$X_2$-$T_{BI}$-, in which:

$T_B$=CO or X, wherein X=O, S, NH, NR, and R is as defined above, $T_B$ is CO when T is —$SO_2NH$—, —$SO_2NR$—, —O—, —S—, —NH—, —N($SO_2R$)—, $T_B$ is X when T is —CO—;

$T_{BI}$=CO or X, in which X is as defined above;

$X_2$ is a divalent radical and is selected from the following compounds:

a)

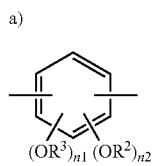

$(OR^3)_{n1}$ $(OR^2)_{n2}$ wherein:

n1 and n2 are integers 0 or 1; $R^2$ and $R^3$ are independently selected from H or $CH_3$;

b)

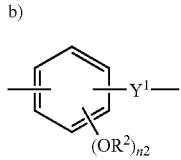

wherein:

n2 and $R^2$ are as above defined;

$Y^1$ is $—CH_2—CH_2—$ or $—CH=CH—(CH_2)_{n2'}—$ wherein n2' is an integer 0 or 1;

c)

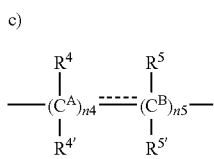

wherein:

n4 is an integer from 1 to 20 and n5 is an integer from 0 to 20, $R^4$ and $R^{4'}$ $R^5$ and $R^{5'}$ are independently selected from H, $CH_3$, OH, $NH_2$, $NHCOCH_3$, COOH; when the bond between the $C^A$ and $C^B$ carbons is a double bond $R^4$ and $R^5$ or R4' and $R^5$ are absent;

C is the bivalent radical $-T_C-Y—$, wherein:

$T_C$=CO, X wherein X is as defined above, or $—(CH_2)_{n6}OC(O)—$ wherein n6 is an integer from 1 to 20, preferably n6 is 1;

Y is a bivalent radical having the following meanings:

d) $—R^1O—$, in which $R^1$ is:

straight or branched $C_1$-$C_{20}$-alkylene eventually containing one or more heteroatoms selected from oxygen, nitrogen, sulphur, or one or more groups $—O(CO)—$, $—NH(CO)—$, $—S(CO)—$, eventually substituted with one or more of the following groups $—OH$, $—SH$, $—NH_2$, $—NHCOR^6$, in which $R^6$ is straight or branched $C_1$-$C_{10}$-alkyl, preferably $CH_3$;

cycloalkylene containing from 5 to 7 carbon atoms into cycloalkylene ring, wherein one or more carbon atoms can be replaced by heteroatoms selected from nitrogen, oxygen or sulphur, and the ring can be substituted with side chains $R^6$, $R^6$ being as defined above;

e)

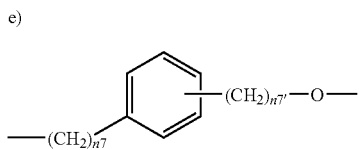

f)

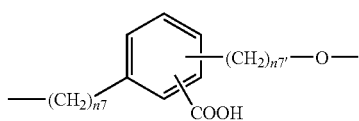

wherein n7 is an integer from 0 to 20, and n7' is an integer from 1 to 20;

g)

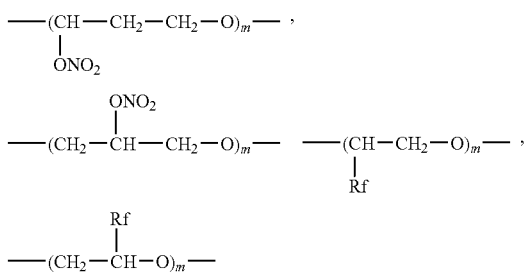

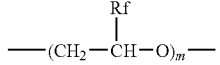

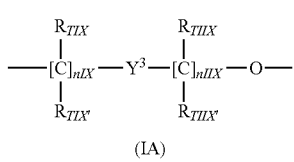

wherein m is an integer from 1 to 6, preferably from 1 to 4, Rf is a hydrogen atom or $CH_3$;

h)

$$—[C]_{nIX}\genfrac{}{}{0pt}{}{R_{TIX}}{R_{TIX'}}—Y^3—[C]_{nIIX}\genfrac{}{}{0pt}{}{R_{TIIX}}{R_{TIIX'}}—O—$$

(IA)

wherein:

nIX is an integer from 0 to 10, preferably from 1 to 5;

nIIX is an integer from 1 to 10, preferably from 1 to 5;

$R_{TIX}$, $R_{TIX'}$, $R_{TIIX}$, $R_{TIIX'}$, are the same or different, and are H or straight or branched $C_1$-$C_4$-alkyl, preferably $R_{TIX}$, $R_{TIX'}$, $R_{TIIX}$, $R_{TIIX'}$ are H;

$Y^3$ is an heterocyclic saturated, unsaturated or aromatic 5 or 6 members ring, containing one or more heteroatoms selected from nitrogen, oxygen, sulphur, and selected from

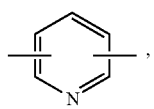
(Y1)

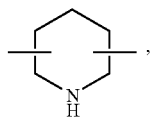
(Y2)

-continued (Y3) 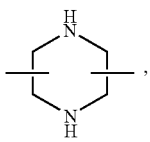

(Y4) 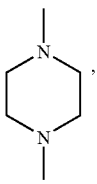

(Y5) 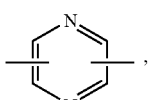

(Y6) 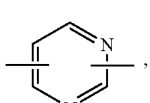

(Y7) 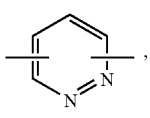

(Y8) 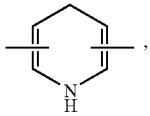

(Y9) 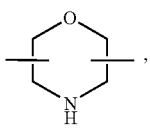

(Y10) 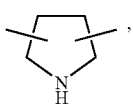

(Y11) 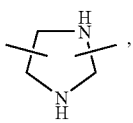

(Y12) 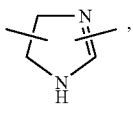

(Y13) 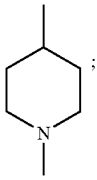

with the proviso that:

when b0=0, c0=1 and T=—SO$_2$NH—, —SO$_2$NR—, —O—, —S—, —NH—, —N(SO$_2$R)— wherein R is as defined above, then T$_C$=(CO) or —(CH$_2$)$_{n6}$O(CO)—;

when b0=0, c0=1 and T=CO then T$_C$=X wherein X is as defined above;

when b0=1 and T=—SO$_2$NH—, —SO$_2$NR—, —O—, —S—, —NH—, —N(SO$_2$R)— wherein R is as defined above, then T$_B$=CO;

when b0=1 and T=CO then T$_B$=X wherein X is as defined above;

when b0=1, c0=1 and T$_{B1}$=CO then T$_C$=X wherein X is as above defined;

when b0=1, c0=1 and T$_{B1}$=X, wherein X is as above defined, then T$_C$=(CO);

when b0=1, c0=0 the T$_{B1}$ has only the meaning of —O—.

Preferred compounds of formula (I) are those wherein b0=0, c0=1, T and T$_C$ are as defined in claim 1, Y is a straight $C_1$-$C_6$ alkylene or

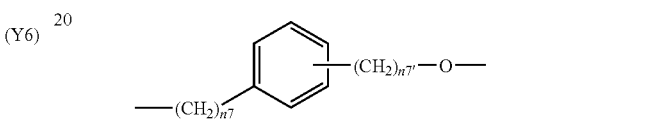

wherein n7 is 0 or 1, and n7' is 1 or 2, or

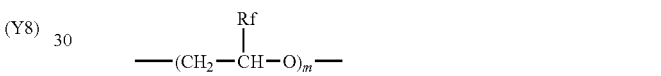

wherein m is 2, Rf is hydrogen.

Particularly preferred compounds of formula (I) are those wherein b0=0, c0=1, T=—N(SO$_2$R)—, T$_C$=CO or —(CH$_2$)$_{n6}$O(CO)— wherein $n_6$=1 and R=CH$_3$ and those wherein b0=0, c0=1, T=—SO$_2$NH— and T$_C$=CO or —(CH$_2$)$_{n6}$O(CO)— wherein $n_6$=1.

Object of the present invention are also pharmaceutical compositions comprising at least a nitro-derivative of cyclooxygenase-2 inhibitors in combination with a pharmaceutically acceptable vehicle and their use in the treatment and/or prophylaxis of inflammatory and cardiovascular disorders, arthritis, rheumatoid arthritis, dysmenhorrea, fever, pain, for treating and/or preventing disorders due to cyclooxygenase-2 elevated levels and for reducing or eliminating the well-known side effects of COX-2 inhibitors.

Test 1

Assay for COX-1 and COX-2 Activities of the Compounds of the Invention.

To a rat liver isolated homogenate in potassium chloride (1.15%) and phosphate buffer (0.1 M, pH 7.4) the compounds under examination were added (dissolved in DMSO 1%) at the 0.5 mM end concentration in homogenate, and the homogenate was maintained at room temperature for 30 minutes, then it was centrifugated (2000 rpm, 5 min) and in surnatant the COX-2 and COX-1 activities as well as the amount of NO released were determined according to the methods described here below.

1-1) In Vitro Evaluation of COX-2 and COX-1 Activities (Human Whole Blood Assays)

The experiments have been carried out according to the procedure described by D. Riendeau et al., The Journal of Pharmacology and Experimental Therapeutics 296:558-566, 2001.

For the evaluation of COX-2 activity, human blood was collected from volunteers, heparin was added (19 U/ml) and several aliquots of 500 µl were incubated with LPS (100 µg/ml) and with 2 µl of solutions (DMSO 1%) of the compounds under examination at different concentrations using 3-fold serial dilutions (1:10, 1:100, 1:1000 e 1:10000) of the above described surnatant or with 2 µl vehicle (DMSO), for 24 h at 37° C. COX-2 activity in the samples has been measured in the plasma after deproteination as PGE2 concentration by radioimmunoassay (Amersham, Oakville, Ontario, Canada).

For the COX-1 assay, an aliquot of 500 µl of human blood was mixed with 2 µl of solutions (DMSO 1%) of the compounds at different concentrations using 3-fold serial dilutions (1:10 1:100 1:1000 and 1:10000) of the above described surnatant or with 2 µl vehicle (DMSO) and blood was allowed to clot for 1 h at 37° C.

COX-1 activity in the samples has been determined in the serum after deproteination as TXB2 levels using an enzyme immunoassay (Cayman Chemicals, Ann Arbor, Mich.).

1-2) Determination of NO Release by Chemiluminescence

An aliquot of the above described surnatant (100 µl) was injected in the reaction chamber of the analyzer containing a reductive solution consisting of glacial acetic acid and potassium iodide. Under these conditions, the nitrates/nitrites present in the sample are converted in NO which is then detected after its reaction with ozone. This reaction produces light, that is detected by photomultipliers and the recorded signal, proportional to the amount of emitted light, allows to quantify nitrates/nitrites present in the sample. For the quantitative determination of the released NO, reference is made to a standard curve obtained with scalar nitrite concentrations.

The compounds meet test 1 when the ratio between COX-1 inhibiting activity and COX-2 inhibiting activity, expressed as $IC_{50}$ is greater than or equal to 5 and release NO in amounts that can be detected by instrument, that is at a concentration equal to or greater than 0.1 µM.

Test 2

Assay for COX-1 and COX-2 Activity of the Precursor Compounds According to the HWBA Method (Human Whole Blood Assays)

The experiments have been carried out using identical procedures as reported by D. Riendeau et al., The Journal of Pharmacology and Experimental Therapeutics 296:558-566, 2001. 2.1 For evaluating COX-2 activity, human blood was collected from volunteers, heparin is added (19 U/ml) and aliquots of 500 µl were incubated with LPS (100 µg/ml) and with 2 µl of solutions (DMSO 1%) of the precursor compounds at different concentrations using 3-fold serial dilutions (1:10, 1:100, 1:1000 and 1:10000) of the highest tested concentration or with 2 µl vehicle (DMSO), for 24 h at 37° C. COX-2 activity in the samples has been determined in the plasma after deproteination as PGE2 concentration using radioimmunoassay (Amersham, Oakville, Ontario, Canada). 2.2 For the evaluation of COX-1 activity, a 500 µl aliquot human blood was mixed with 2 µl of solutions (DMSO 1%) of the precursor compounds at different concentrations using 3-fold serial dilutions (1:10, 1:100, 1:1000 and 1:10000) of the highest tested concentration or with 2 µl vehicle (DMSO) and the blood was allowed to clot for 1 h at 37° C.

COX-1 activity in the samples was determined in the plasma after deproteination as TXB2 concentration using enzyme immunoassay (Cayman Chemicals, Ann Arbor, Mich.).

Test 2 is met by those precursor compounds having a COX-1 inhibiting activity/COX-2 inhibiting activity ratio, expressed as $IC_{50}$, greater than or equal 5.

The precursors that can be employed for the preparation of the compounds object of the present invention are described in the following patents or patent applications: WO 91/19708, WO 94/13635, WO 94/15932, WO 94/20480, WO 94/26731, WO 94/27980, WO 95/00501, WO 95/11883, WO 95/15315, WO 95/15316, WO 95/15317, WO 95/15318, WO 95/18799, WO 95/21817, WO 95/30652, WO 95/30656, WO 96/03392, WO 96/03385, WO 96/03387, WO 96/03388, WO 96/06840, WO 96/09293, WO 96/09304, WO 96/10021, WO 96/13483, WO 96/16934, WO 96/19462, WO 96/19463, WO 96/19469, WO 96/21667, WO 96/23786, WO 96/24584, WO 96/24585, WO 96/25405, WO 96/31509, WO 96/36617, WO 96/36623, WO 96/37467, WO 96/37468, WO 96/37469, WO 96/38418, WO 96/38442, WO 96/41626, WO 96/41645, WO 97/03953, WO 97/11704, WO 97/13755, WO 97/13767, WO 97/14691, WO 97/16435, WO 97/25045, WO 97/27181, WO 97/28120, WO 97/28121, WO 97/29776, WO 97/34882, WO 97/36863, WO 97/37984, WO 97/38986, WO 97/40012, WO 97/41100, WO 97/44027, WO 97/44028, WO 97/45420, WO 98/00416, WO 98/03484, WO 98/04527, WO 98/05639, WO 98/06708, WO 98/07714, WO 98/11080, WO 98/14205, WO 98/21195, WO 98/22442, WO 98/32732, WO 98/33769, WO 98/39330, WO 98/41511, WO 98/41516, WO 98/43966, WO 98/43649, WO 98/46594, WO 98/47509, WO 98/47871, WO 98/47890, WO 98/50033, WO 98/50075, WO 98/52937, WO 98/57924, WO 99/05104, WO 99/10331, WO 99/10332, WO 99/11605, WO 99/12930, WO 99/13799, WO 99/14194, WO 99/14195, WO 99/15205, WO 99/15503, WO 99/15513, WO 99/15505, WO 99/18960, WO 99/20110, WO 97/27181, WO 97/28120, WO 97/28121, WO 97/29776, WO 97/34882, WO 97/36863, WO 97/37984, WO 97/38986, WO 97/40012, WO 97/41100, WO 97/44027, WO 97/44028, WO 97/45420, WO 98/00416, WO 98/03484, WO 98/04527, WO 98/05639, WO 98/06708, WO 98/07714, WO 98/11080, WO 98/14205, WO 98/21195, WO 98/22442, WO 98/32732, WO 98/33769, WO 98/39330, WO 98/41511, WO 98/41516, WO 98/43966, WO 98/43649, WO 98/46594, WO 98/47509, WO 98/47871, WO 98/47890, WO 98/50033, WO 98/50075, WO 98/52937, WO 98/57924, WO 99/05104, WO 99/10331, WO 99/10332, WO 99/11605, WO 99/12930, WO 99/13799, WO 99/14194, WO 99/14195, WO 99/15205, WO 99/15503, WO 99/15513, WO 99/15505, WO 99/18960, WO 99/20110, WO 99/20589, WO 99/21585, WO 99/22720, WO 99/23087, WO 99/25695, WO 99/33796, WO 99/35130, WO 99/41224, WO 99/45913, WO 99/55830, WO 99/59634, WO 99/59635, WO 99/61016, WO 99/61436, WO 99/62884, WO 99/64415, WO 00/00200, WO 00/01380, WO 00/08024, WO 00/10993, WO 00/13685, WO 00/23433, WO 00/24719, WO 00/25779, WO 00/26216, WO 00/27382, WO 00/29022, WO 00/29023, WO 00/37107, WO 00/38730, WO 00/38786, WO 00/40087. WO 00/48583, WO 00/51685, WO 00/52008, WO 00/53149, WO 00/68215, WO 01/70704, WO 01/15138, WO 01/68633, EP 0087629, EP 0418845, EP 0554829, EP 0745596, EP 0788476, EP 0826676, EP 0863134, EP 0882016, EP 0927555, EP 0937722, EP 1006114, U.S. Pat. No. 3,840,597, U.S. Pat. No. 5,134,142, U.S. Pat. No. 5,344,991, U.S. Pat. No. 5,380,738, U.S. Pat. No. 5,393,790, U.S. Pat. No. 5,399,357, U.S. Pat. No. 5,434, 178, U.S. Pat. No. 5,409,944, U.S. Pat. No. 5,436,265, U.S. Pat. No. 5,466,823, U.S. Pat. No. 5,474,995, U.S. Pat. No. 5,475,021, U.S. Pat. No. 4,486,534, U.S. Pat. No. 5,504,215, U.S. Pat. No. 5,508,426, U.S. Pat. No. 5,510,368, U.S. Pat. No. 5,510,496, U.S. Pat. No. 5,516,907, U.S. Pat. No. 5,521, 207, U.S. Pat. No. 5,521,213, U.S. Pat. No. 5,536,752, U.S. Pat. No. 5,550,142, U.S. Pat. No. 5,552,422, U.S. Pat. No.

5,563,165, U.S. Pat. No. 5,580,985, U.S. Pat. No. 5,585,504, U.S. Pat. No. 5,596,008, U.S. Pat. No. 5,604,253, U.S. Pat. No. 5,604,260, U.S. Pat. No. 5,616,601, U.S. Pat. No. 5,620,999, U.S. Pat. No. 5,633,272, U.S. Pat. No. 5,639,780, U.S. Pat. No. 5,643,933, U.S. Pat. No. 5,668,161, U.S. Pat. No. 5,677,318, U.S. Pat. No. 5,686,170, U.S. Pat. No. 5,686,460, U.S. Pat. No. 5,691,374, U.S. Pat. No. 5,696,143, U.S. Pat. No. 5,698,584, U.S. Pat. No. 5,700,816, U.S. Pat. No. 5,710,140, U.S. Pat. No. 5,719,163, U.S. Pat. No. 5,733,909, U.S. Pat. No. 5,753,688, U.S. Pat. No. 5,756,530, U.S. Pat. No. 5,760,068, U.S. Pat. No. 5,783,597, U.S. Pat. No. 5,789,413, U.S. Pat. No. 5,807,873, U.S. Pat. No. 5,817,700, U.S. Pat. No. 5,840,746, U.S. Pat. No. 5,840,924, U.S. Pat. No. 5,849,943, U.S. Pat. No. 5,859,257, U.S. Pat. No. 5,861,419, U.S. Pat. No. 5,883,267, U.S. Pat. No. 5,908,852, U.S. Pat. No. 5,908,858, U.S. Pat. No. 5,925,631, U.S. Pat. No. 5,935,990, U.S. Pat. No. 5,945,539, U.S. Pat. No. 5,972,986, U.S. Pat. No. 5,981,576, U.S. Pat. No. 5,985,902, U.S. Pat. No. 5,990,148, U.S. Pat. No. 5,994,379, U.S. Pat. No. 5,994,381, U.S. Pat. No. 6,001,843, U.S. Pat. No. 6,002,014, U.S. Pat. No. 6,020,343, U.S. Pat. No. 6,025,353, U.S. Pat. No. 6,028,072, U.S. Pat. No. 6,046,191, U.S. Pat. No. 6,071,936, U.S. Pat. No. 6,071,954, U.S. Pat. No. 6,077,869, U.S. Pat. No. 6,080,876, U.S. Pat. No. 6,083,969, U.S. Pat. No. 6,136,839, U.S. Pat. No. 5,681,842, U.S. Pat. No. 5,776,967, U.S. Pat. No. 5,824,699, U.S. Pat. No. 5,883,267, U.S. Pat. No. 5,905,089, U.S. Pat. No. 5,908,858, U.S. Pat. No. 5,945,538, U.S. Pat. No. 5,980,905, U.S. Pat. No. 5,994,381, U.S. Pat. No. 6,004,948, US 2002/0058690 and JP 2001139575.

Examples of preferred COX-2 selective inhibitors of formula M-TH or M-TOH are listed here below:

4-(5-methyl-3-phenylisoxazol-4-yl)benzenesulfonamide (Valdecoxib), 4-[5-(4-methylphenyl)-3-(trifluoromethyl)-1H-pyrazol-1-yl]benzenesulfon-amide (Celecoxib), 4-(4-cyclohexyl-2-methyloxazol-5-yl)-2-fluoro-benzenesulfonamide (Tilmacoxib), N-[6-[(2,4-difluorophenyl)thio]-2,3-dihydro-1-oxo-1H-inden-5-yl]-methanesulfonamide (L-745337), N-(4-nitro-2-fenoxyphenyl)methanesulfonanilide, N-(4-nitro-2-cycloexyloxy-phenyl)methanesulfonanilide, 2-[(2-chloro-6-fluorophenyl)amino]-5-methylbenzeneacetic acid (COX189), 2-[(2-chloro-6-fluorophenyl)-amino]-4-methylbenzeneacetic acid.

Preferred drugs of formula (I) according to the invention are:

N-(6-(2,4-difluorophenyl)thio-2,3-dihydro-1-oxo-1-inden-5-yl)-N-(4-nitrooxy)butyroyloxymethyl)methanesulfonamide, N-(6-(2,4-difluoro-phenyl)thio)-2,3-dihydro-1-oxo-1-inden-5-yl)-N-(3-nitrooxymethyl)-benzoyloxymethyl)methanesulfonamide, (Z)-2-(4-methylsul-fonyl)phenyl)-3-phenyl-2-buten-1,4-diol-1-((4-nitrooxymethyl)benzoate), N-(4-(5-(4-methylphenyl)-3-(trifluoromethyl)-1H-pyrazol-1-yl)phenylsulfonyl-4-nitrooxybutanamide, N-(3-nitrooxymethyl)benzoyl-oxymethyl-N-(2-phenoxy-4-nitrophenyl)methanesulfonamide.

As a few compounds of formula (I) possess one or more asymmetrical carbon atoms, they can exist as optically pure enantiomers, pure diastereomers, enantiomer mixtures, diastereomers mixtures, enantiomer racemic mixtures, racemates or racemate mixtures. The object of the invention are also all these stereoisomers as well mixtures thereof. Compounds of the invention comprise a carbon-carbon double bond may exist as E or Z geometrical isomers, it is to be understood that the present invention includes all these isomers as well mixtures thereof.

As mentioned above, object of the present invention are also pharmaceutical compositions containing at least a compound of the present invention of formula (I) together with non toxic adjuvants and/or vehicles usually employed in the pharmaceutical field.

The daily dose of active ingredient that should be administered can be a single dose or it can be an effective amount divided into several smaller doses that are to be administered throughout the day. Usually, total daily dose may be in amounts from 1 to 2000 mg, preferably from 10 to 1000 mg, in particular from 50 to 500 mg. The dosage regimen and administration frequency for treating the mentioned diseases with the compound of the invention and/or with the pharmaceutical compositions of the present invention will be selected in accordance with a variety of factors, including for example age, body weight, sex and medical condition of the patient as well as severity of the disease, route of administration pharmacological considerations and eventual concomitant therapy with other drugs. In some instances, dosage levels below or above the aforesaid range and/or more frequent may be adequate, and this logically will be within the judgment of the physician and will depend on the disease state.

The compounds of the invention may be administered orally, parenterally, rectally or topically, by inhalation or aerosol, in formulations eventually containing conventional non-toxic pharmaceutically acceptable carriers, adjuvants and vehicles as desired. Topical administration may also involve the use of transdermal administration such as transdermal patches or ionophoresis devices. The term "parenteral" as used herein, includes subcutaneous injections, intravenous, intramuscular, intrasternal injection or infusion techniques.

Injectable preparations, for example sterile injectable aqueous or oleaginous suspensions may be formulated according to known art using suitable dispersing or wetting agents and suspending agents. The sterile injectable preparation may also be a sterile injectable solution or suspension in a non-toxic parenterally acceptable diluent or solvent. Among the acceptable vehicles and solvents are water, Ringer's solution and isotonic sodium chloride. In addition, sterile, fixed oils are conventionally employed as a solvent or suspending medium. For this purpose any bland fixed oil may be employed including synthetic mono or diglycerides, in addition fatty acids such as oleic acid find use in the preparation of injectables.

Suppositories for rectal administration of the drug can be prepared by mixing the active ingredient with a suitable non-irritating excipient, such as cocoa butter and polyethylene glycols.

Solid dosage forms for oral administration may include capsules, tablets, pills, powders, granules and gels. In such solid dosage forms, the active compound may be admixed with at least one inert diluent such as sucrose, lactose or starch. Such dosage forms may also comprise, as in normal practice, additional substances other than inert diluents, e.g. lubricating agents such as magnesium stearate. In the case of capsules, tablets and pills, the dosage forms may also comprise buffering agents. Tablets and pills can additionally be prepared with enteric coatings.

Liquid dosage forms for oral administration may include pharmaceutically acceptable emulsions, solutions, suspensions, syrups and elixirs containing inert diluents commonly used in the art, such as water. Such compositions may also comprise adjuvants, such as wetting agents, emulsifying and suspending agents, and sweetening, flavoring and the like.

The synthesis methods of the precursor drugs are reported in the publications mentioned above. The precursor compounds of B described above are compounds available on the market or they can be obtained according to methods well-known in the art and described for example in "The Merck Index" 13th Ed. (2001). The precursors of Y having the formula (IA), wherein the free valence of oxygen is saturated with H and the free valence of carbon is saturated with a carboxylic, hydroxy or amine group, are products available on the market or they can be prepared according to methods well known in the art.

Generally, the nitrooxyderivatives of the present invention may be synthetized using methods known form literature or as reported in the following patents or patent applications in the name of Applicant: EP 722434, EP 759899, WO 00/51988, WO 00/61537, WO 00/61541.

A) The compounds of formula (I) as above defined wherein T is —N(SO$_2$R), b0=0, c0=1, T$_C$=—(CH$_2$)$_{n6}$O(CO)—, wherein R, Y, are as defined above and n6=1 are obtained by reacting a compound of formula (II)

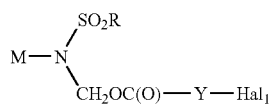
(II)

wherein M, R, are as defined above Y has one of meanings mentioned above wherein the oxygen terminal atom is absent and replaced by an halogen atom Hal$_1$ in formula (II), and Hal, is an halogen atom, preferably Br or Cl, with AgNO$_3$.

The reaction is carried out in a suitable organic solvent, such as acetonitrile or THF at a temperature of from 0° to 80° C.

The compounds of formula (II) as above defined are obtained by reacting a compound of formula (III)

M-NSO$_2$R$^-$Na$^+$ (III)

wherein M, R, are as defined above with a compound of formula (IV)

Hal-CH$_2$OC(O)—Y-Hal$_1$ (IV)

wherein Hal is an Halogen atom, Hal and Hal$_1$ my have the same or a different meaning, Y has one of meanings mentioned above wherein the oxygen terminal atom is absent and replaced by an halogen atom Hal$_1$ in formula (IV).

The reaction is carried out in a suitable solvent, such as dry THF at a temperature of from 0° to 80°.

The compounds of formula (III) are commercially available compounds or may be obtained by salifying the corresponding secondary sulfonamide groups by well known reactions or can be obtained by well known reactions described in the patents or patent applications reported above.

The compounds of formula (IV) are commercially available compounds or may be obtained from known compounds by known reactions.

B) The compounds of formula (I) as above defined wherein T=—SO$_2$NH, b0=0, c0=1, T$_c$=CO wherein M, Y, are as defined above are obtained by reacting a compound of formula (V)

M-SO$_2$NH—C(O)—Y-Hal$_1$ (V)

wherein M is as defined above, Y has one of meanings mentioned above wherein the oxygen terminal atom is absent and replaced by an halogen atom Hal$_1$ in formula (V), and Hal$_1$ is an halogen atom, preferably Br or Cl, with AgNO$_3$.

The reaction is carried out in a suitable organic solvent, such as acetonitrile or THF at a temperature of from 0° to 80° C.

The compounds of formula (V) as above defined are obtained by reacting a compound of formula (VI)

M-SO$_2$NH$_2$ (VI)

wherein M is as defined above with a compound of formula (VII) or the corresponding anhydride of formula (VIII)

Hal-C(O)—Y-Hal$_1$ (VII)

or (Hal$_1$-Y—CO)$_2$ (VIII)

wherein Hal$_1$ is as defined above, Hal is an Halogen atom, Hal and Hal$_1$ my have the same or a different meaning, Y has one of meanings mentioned above wherein the oxygen terminal atom is absent and replaced by an halogen atom Hal$_1$ in formulas (VI) and (VII).

The reaction is carried out in a suitable solvent, such as for example THF or DMF at a temperature of from 0° to 80°.

The compounds of formula (VI) are commercially available compounds or can be obtained by well known reactions described in the patents or patent applications reported above.

The compounds of formula (VII) and (VIII) are commercially available compounds or may be obtained from known compounds by known reactions.

The invention will now be described in greater detail by reference to the following non-limiting examples.

EXAMPLE 1

N-[6-(2,4-Difluorophenyl)thio)-2,3-dihydro-1-oxo-1-inden-5-yl]-N-[4-(nitrooxy)butyroyloxymethyl]-methanesulfonamide

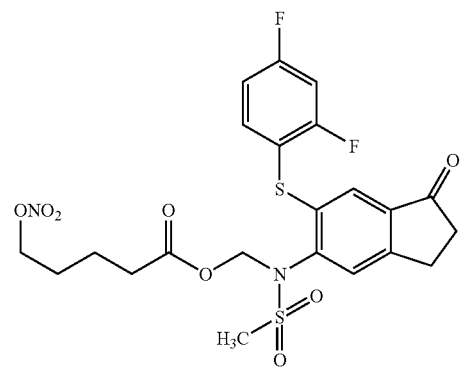

1.A) N-[6-(2,4-difluorophenyl)thio]-2,3-dihydro-1-oxo-1-inden-5-yl]-N-[4-(chloro)butyroyloxymethyl] methanesulfonamide (1A)

A solution of chloromethyl (4-chloro)butyrate (1 g, 5.40 mmol) in anhydrous tetrahydrofurane (5 ml) was slowly added dropwise in a suspension of N-[6-(2,4-difluorophenyl) thio]-2,3-dihydro-1-oxo-1-inden-5-yl]-methanesulfonamide sodium salt (2.04 g, 5.40 mmol) in anhydrous tetrahydrofurane (25 ml). The reaction was allowed to stand under stirring overnight at room temperature. The solvent was evaporated under vacuum, the residue was treated with methylene chloride (40 ml) and the solution thus obtained was washed with a 5% sodium bicarbonate solution and then with water. The organic phase was dried on sodium sulphate. The crude product was purified by chromatography on a silica gel column with n-hexane/ethyl acetate 8/2 as eluent to give 1.12 g of the desired product.

1.B) N-[6-(2,4-difluorophenyl)thio]-2,3-dihydro-1-oxo-1-inden-5-yl]-N-[4-(nitrooxy)butyroyloxymethyl]-methanesulfonamide A solution of product 1A (1 g, 1.98 mmol) in acetonitrile (20 ml) was added with silver nitrate (0.67 g, 3.96 mmol). The solution was heated at 80° C. for 15 hours in absence of light. The silver salts were filtered off and solvent was evaporated under vacuum. The crude product thus obtained was purified by chromatography on a silica gel column with n-hexane/ethyl acetate 8/2 as eluent to give 503 mg of the title product.
Elemental Analysis
Calculated: C, 48.64%; H, 4.27%; F, 7.32%; S, 12.37%.
Found: C, 48.57%; H, 4.03%; F, 7.31%; S, 12.33%.

EXAMPLE 2

N-[6-(2,4-Difluorophenyl)thio]-2,3-dihydro-1-oxo-1-inden-5-yl]-N-[3-(nitrooxymethyl)benzoyloxymethyl]methanesulfonamide

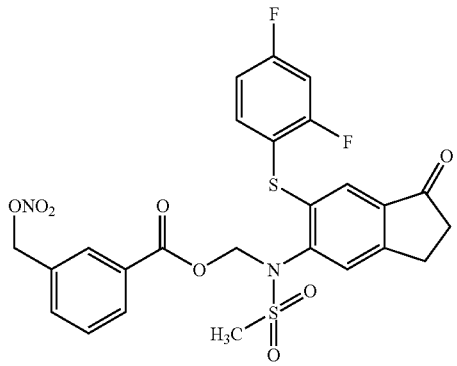

2.A) N-[6-(2,4-difluorophenyl)thio]-2,3-dihydro-1-oxo-1-inden-5-yl]-N-[3-(chloromethyl)benzoyloxymethyl]methanesulfonamide (2A)

A solution of chloromethyl (3-chloromethyl)benzoate (1.5 g, 6.80 mmol) in anhydrous tetrahydrofurane (7 ml) was slowly added dropwise in a suspension of N-[6-(2,4-difluorophenyl)thio]-2,3-dihydro-1-oxo-1-inden-5-yl]methanesulfonamide sodium salt (2.57 g, 6.80 mmol) in anhydrous tetrahydrofurane (45 ml). The reaction was allowed to stand under stirring overnight at room temperature. The solvent was evaporated under vacuum, the residue was treated with methylene chloride (60 ml) and the solution thus obtained was washed with a solution of 5% sodium bicarbonate and then with water. The organic phase was dried on sodium sulphate. The crude product thus obtained was purified by chromatography on silica gel column with n-hexane/ethyl acetate 8/2 as eluent to give 1.31 g of the desired product.

2.B) N-[6-(2,4-difluorophenyl)thio]-2,3-dihydro-1-oxo-1-inden-5-yl]-N-[3-(nitrooxymethyl)benzoyloxymethyl]-methanesulfonamide A solution of product 2A (1 g, 1.86 mmol) in acetonitrile (20 ml) was added with silver nitrate (0.47 g, 2.78 mmol). The solution was heated at 80° C. for 15 hours in absence of light. The silver salts were filtered off and the solvent was evaporated under vacuum. The crude product thus obtained was purified by chromatography on a silica gel column with n-hexane/ethyl acetate as eluent 8/2 to give 623 mg of title compound.
Elemental Analysis
Calculated: C, 53.19%; H, 3.56%; F, 6.73%; S, 11.60%.
Found: C, 53.27%; H, 3.43%; F, 6.79%; S, 11.5%.

EXAMPLE 3

(Z)-2-(4-Methylsulphonylphenyl)-3-fenyl-2-buten-1,4-diol-1-[(4-nitrooxymetyl)benzoate]

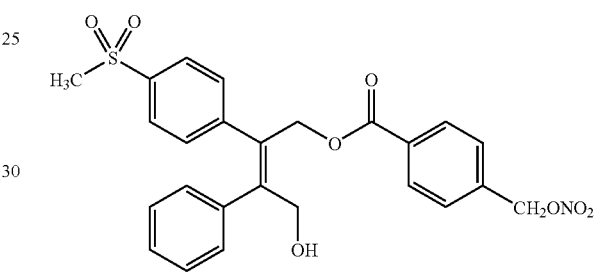

3.A) (Z)-2-(4-methylsulphonylphenyl)-3-phenyl-2-buten-1,4-diol

A solution of 1M DIBAL in toluene (185 ml) was slowly added into a solution of 3-[phenyl-4-(4-methylsulphonyl)phenyl]-2-(5H)-furanone (18.1 g, 57.1 mmol) in tetrahydrofurane (750 ml).
The solution was allowed to stand under stirring at 0° C. for 90 minutes, then overnight at room temperature. Into the reaction mixture cooled at 0° C. a 1M solution of sodium potassium tartrate was added dropwise. The solution was extracted with ethyl acetate and the organic phase was washed with water and dried with sodium sulphate to give 15 g of the desired compound.

3.B) (Z)-2-(4-methylsulphonylphenyl)-3-phenyl-2-buten-1,4-diol-1-[(4-chloromethyl)benzoate] (3B)

A solution of (Z)-2-(4-mehylsulphonylphenyl)-3-phenyl-2-butene-1,4-diol (15 g, 46.7 mmol), triethylamine (13.3 ml, 95.7 mmol) and 4-dimethylaminopyridine (0.76 g, 6.26 mmol) in methylene chloride (30 ml), cooled at 0° C., was slowly added with a solution of 4-chloromethyl benzoyl chloride (8.8 g, 46.7 mmol) in methylene chloride (30 ml). The reaction mixture was allowed to stand under stirring for 30 min and then acidified with 1N HCl (100 ml). The separated organic phase was dried with sodium sulphate and concentrated under vacuum. The crude compound thus obtained was purified by chromatography on a silica gel column with n-hexane/ethyl acetate 8/2 as eluent to give 4.3 g of the title compound.

3.C) (Z)-2-(4-methylsulphonylphenyl)-3-phenyl-2-buten-1,4-diol-1-[(4-nitrooxymethyl)benzoate]

To a solution of product 3B (3 g, 6.38 mmol) in acetonitrile (60 ml) silver nitrate was added (1.07 g, 6.38 mmol). The solution was heated at 50° C. for 8 ore in absence of light. The silver salts were filtered off and the solvent was evaporated under vacuum. The crude product thus obtained was purified by chromatography on a silica gel column with n-hexane/ethyl acetate 8/2 as eluent to give 1.3 g of the title compound.

Elemental Analysis
Calculated: C, 60.36%; H, 4.65%; S, 6.43%.
Found: C, 60.40%; H, 4.63%; S, 6.33%.

EXAMPLE 4

Synthesis of N-[4-[5-(4-methylphenyl)-3-(trifluoromethyl)-1H-pyrazol-1-yl]phenylsulfonyl]-4-nitrooxy-butanamide

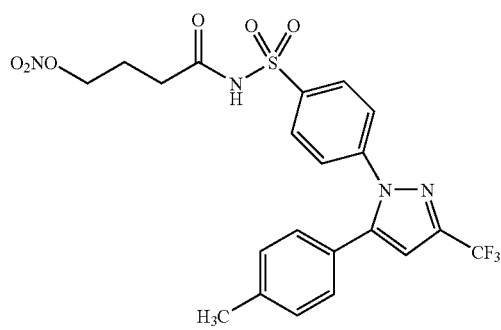

4.A) N-[4-[5-(4-methylphenyl)-3-(trifluoromethyl)-1H-pyrazol-1-yl]phenylsulfonyl]4-chlorobutanamide (4A)

At a solution of N-[4-[5-(4-methylphenyl)-3-(trifluoromethyl)-1H-pyrazol-1-yl]phenylsulfonyl]benzensulfonamide (1 g, 2.262 mmol) in pyridine (50 ml) cooled at 0° C., 4-chlorobutyrylchloride was added dropwise (0.294 ml), the solution was maintained under stirring for 10 minutes at 0° C., the temperature was then raised to room temperature and the solution was maintained under stirring for 2 hours. Then HCl was added (50 ml, 0.1 N) and the mixture was extracted with CH$_2$Cl$_2$. The combined organic phases were washed with water, dried and the solvent was evaporated at reduced pressure. The crude compound as purified by chromatography on a silica gel column with n-hehan/ethyl acetate 8/2 as eluent to give 0.400 mg of product 4A.

4.B) N-[4-[5-(4-methylphenyl)-3-(trifluoromethyl)-1H-pyrazol-1-il]phenylsulfonyl]-4-nitrooxybutanamide To a solution of product 4A (0.380 g, 0.78 mmol) in acetonitrile (5 ml) silver nitrate was added (0.265 g, 1.56 mmol) and the solution was heated for 8 hours at 50° C. in absence of light. The silver salts were filtered off and the solvent was evaporated at reduced pressure. The crude product thus obtained was purified by chromatography on a silica gel column with n-hexane/ethyl acetate 8/2 as eluent to give 0.4 g of the title compound.

Elemental Analysis:

| Calculated: | C 49.22%; | H 3.74%; | S 6.26% | F 11.12% |
|---|---|---|---|---|
| Found: | C 49.26%; | H 3.77%; | S 6.28% | F 11.09% |

EXAMPLE 5

Synthesis of N-[(3-nitrooxymethyl)benzoyloxymethyl]-N-(2-phenoxy-4-nitrophenyl)methanesulfonamide

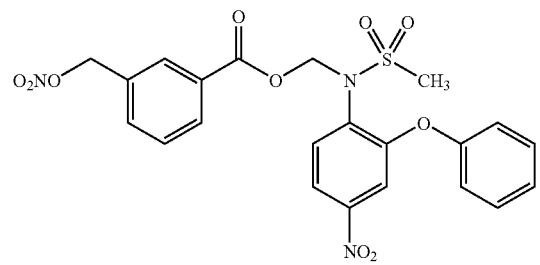

5.A) N-[(3-chloromethyl)benzoyloxymethyl]-N-(2-phenoxy-4-nitrophenyl)methanesulfonamide (5A)

A solution of chloromethyl 3-chloromethylbenzoate (1.5 g, 6.80 mmol) in anhydrous tetrahydrofurane (7 ml) was slowly added dropwise in a suspension of N-(2-phenoxy-4-nitrophenyl)methanesulfonamide sodium salt (2.25 g, 6.80 mmol) in anhydrous tetrahydrofurane (45 ml). The reaction was allowed to stand overnight under stirring at room temperature. The solvent was evaporated at reduced pressure, the residue was dissolved in methylene chloride (60 ml) and the solution thus obtained was washed with a 5% sodium bicarbonate solution and then with water. The organic phase was dried on sodium sulphate. The crude product thus obtained was purified by chromatography on a silica gel column with n-hexane/ethyl ether 7/3 as eluent to give 0.830 g of product 5A.

5. B) N-[6-(2,4-difluorophenyl)thio]-2,3-dihydro-1-oxo-1-inden-5-yl]-N-[3-(nitrooxymethyl)benzoyloxymethyl]methanesulfonamide To a solution of product 5A (0.8 g 1.63 mmol) in acetonitrile (20 ml) Silver nitrate was added (0.55 g, 0.32 mmol). The solution was heated at 80° C. for 15 hours in absence of light. The silver salts were filtered off and the solvent was evaporated under vacuum. The crude product thus obtained was purified by chromatography on a silica gel column with n-hexane/diethyl ether 8/2 to give 0.330 g of the desired product.

$^1$H NMR(CDCl$_3$) ppm: 3.26 (3H, s); 5.98 (2H, s); 5.5 (2H, s); 6.98-8.01 (17H, m).

EXAMPLE F1

Comparison of Gastric Tolerability and Blood Pressure Effect of the Compounds of the Invention Vs Precursor Compound The experiment was carried out according to the method described by M. N. Muscarà et al. Br. J. Pharmacol. 133, 1314, 2001, and employing groups of 10 rats weighing each 200-250 g.

The compounds, suspended in 1% carboxymethylcellulose, were administered orally for two weeks at a daily dose of 10 mg/kg body weight.

Hypertension was induced by addition of L-NAME (N-omega-nitro-L-arginine methylester) to the drinking water at a concentration of 400 mg/liter. At the end of the treatment, the blood pressure was determined by introduction of a cannula into femoral artery and measurement with polygraphic transducer, 16 hours after the last administration. The animals were then sacrificed and the eventual gastric damage was revealed.

The results show that the product object of the invention described in example 4, N-[4-[5-(4-methylphenyl)-3-(trifluoromethyl)-1H-pyrazol-1-yl]phenylsulphonyl]-4-nitrooxybutanamide, is well tolerated without no increase of the blood pressure. At contrary, the reference COX-2 inhibitor celecoxib causes a gastric damage into 80% of the treated animals and an increase of the blood pressure on an average of 15 mmHg.

The invention claimed is:

1. A compound of formula (I) or a salt thereof

M-T-Y$_A$—NO$_2$     (I)

wherein:
M-T is the residue of 4-[5-(4-methylphenyl)-3-(trifluoromethyl)-1H-pyrazol-1-yl]benzenesulfonamide, wherein T=—SO$_2$NH—, and
Y$_A$=—(B)$_{b0}$-(T$_C$-Y)$_{c0}$— wherein:
b0 and c0 are the integers 1 or 0, with the proviso that b0 and c0 cannot be simultaneously 0,
B=-T$_B$-X$_2$-T$_{BI}$-, in which:
T$_B$=CO;
T$_{BI}$=CO or X, in which X is O, S, NH, or NR, wherein R is an alkyl with 1-10 carbon atoms;
X$_2$ is a divalent radical and is selected from the following compounds:

a)

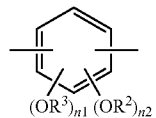

wherein:
n1 and n2 are integers 0 or 1; R$^2$ and R$^3$ are independently selected from H or CH$_3$;

b)

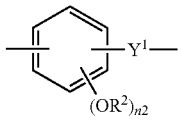

wherein:
n2 and R$^2$ are as above defined;
Y$^1$ is —CH$_2$—CH$_2$— or —CH=CH—(CH$_2$)$_{n2'}$— wherein n2' is an integer 0 or 1;

c)

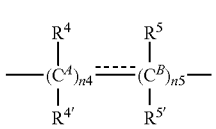

wherein:
n4 is an integer from 1 to 20 and n5 is an integer from 0 to 20; R$^4$, R$^{4'}$, R$^5$ and R$^{5'}$ are independently selected from the group consisting of H, CH$_3$, OH, NH$_2$, NHCOCH$_3$, and COOH; when the bond between the C$^A$ and C$^B$ carbons is a double bond, then R$^4$ and R$^5$ or R$^{4'}$ and R$^{5'}$ are absent;
T$_C$=CO, X wherein X is as defined above, or —(CH$_2$)$_{n6}$OC(O)— wherein n6 is an integer from 1 to 20;
Y is a bivalent radical having the following meanings:
d) —R$^1$O—, in which R$^1$ is:
straight or branched C$_1$-C$_{20}$-alkylene optionally containing one or more heteroatoms selected from oxygen, nitrogen, sulphur, or one or more groups —O(CO)—, —NH(CO)—, —S(CO)—, optionally substituted with one or more of the following groups —OH, —SH, —NH$_2$, —NHCOR$^6$, in which R$^6$ is straight or branched C$_1$-C$_{10}$-alkyl;
cycloalkylene containing from 5 to 7 carbon atoms into cycloalkylene ring, wherein one or more carbon atoms can be replaced by heteroatoms selected from nitrogen, oxygen or sulphur, and the ring can be substituted with side chains R$^6$, R$^6$ being as defined above;

e)

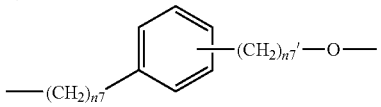

f)

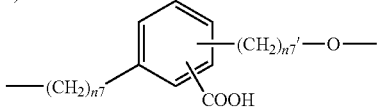

wherein n7 is an integer from 0 to 20, and n7' is an integer from 1 to 20;

g)

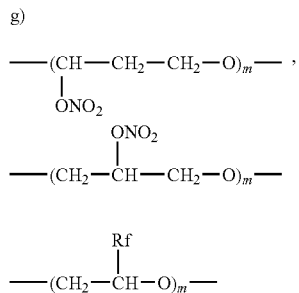

wherein m is an integer from 1 to 6, Rf is a hydrogen atom or $CH_3$;

h)

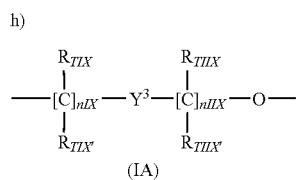

(IA)

wherein:

nIX is an integer from 0 to 10;

nIIX is an integer from 1 to 10;

$R_{TIX}$, $R_{TIX'}$, $R_{TIIX}$, $R_{TIIX'}$ are the same or different, and are H or straight or branched $C_1$-$C_4$-alkyl;

$Y^3$ is selected from the group consisting of:

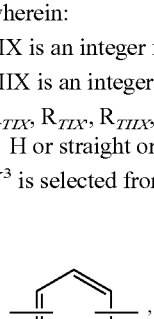
(Y1)

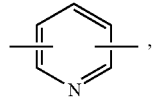
(Y2)

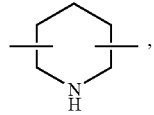
(Y3)

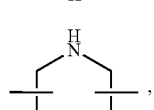
(Y4)

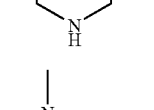
(Y5)

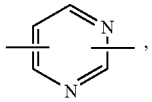
(Y6)

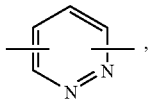
(Y7)

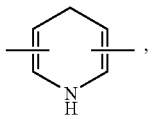
(Y8)

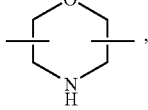
(Y9)

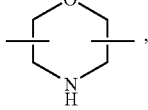
(Y10)

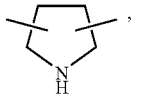
(Y11)

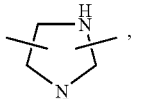
(Y12), and

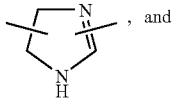
(Y13);

with the proviso that:

when b0=0, and c0=1, then $T_C$=(CO) or —$(CH_2)_{n6}$O(CO)—;

when b0=1, then $T_B$=CO;

when b0=1, c0=1 and $T_{B1}$=CO then $T_C$=X wherein X is as above defined;

when b0=1, c0=1 and $T_{B1}$=X, wherein X is as above defined, then $T_C$=(CO);

when b0=1, c0=0 the $T_{B1}$ has only the meaning of —O—.

2. A compound of formula (I) according to claim 1 wherein b0=0, c0=1, T and $T_C$ are as defined in claim 1, Y is a straight $C_1$-$C_6$ alkylene or

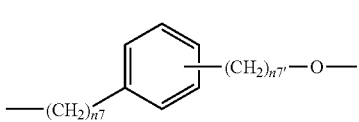

wherein n7 is 0 or 1, and n7' is 1 or 2, or

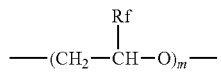

wherein m is 2, Rf is hydrogen.

3. A compound of formula (I) according to claim 2 wherein b0=0, c0=1, T=-SO$_2$NH— and T$_c$=CO or (CH$_2$)$_{n6}$O(CO)— wherein n6=1.

4. A compound according to claim 3, that is N-[4-[5-(4-methylphenyl)-3-(trifluoromethyl)-1H-pyrazol-1-yl]phenyl-sulfonyl]-4-nitrooxybutanamide.

5. A compound of formula (I) or a salt thereof according to claim 1, wherein said compound is a therapeutic agent.

6. A method of treatment of pain, fever and inflammatory disorders selected from the group consisting of: arthritis, rheumatoid arthritis, osteoarthritis, dysmenhorrea, allergic rhinitis, sinusitis, chronic obstructive pulmonary diseases, dermatitis, psoriasis, cystic fibrosis, multiple sclerosis, vasculitis and organ transplant rejection, comprising administering to a subject a compound of formula (I) or a salt thereof according to claim 1.

7. A method of treatment of cardiovascular diseases selected from the group consisting of: atherosclerosis, restenosis, coronary artery disease, angina, diabetes mellitus, diabetic nephropathy, diabetic retinopathy, stroke and myocardic infarct, comprising administering to a subject a compound of formula (I) or a salt thereof according to claim 1.

8. A method of treatment of gastrointestinal disorders selected from the group consisting of: inflammatory intestinal disorders, Crohn's disease, gastritis, ulcerative colitis, peptic ulcer, haemorrhagic ulcer, gastric hyperacidity, dyspepsia, gastroparesis, Zollinger-Ellison's syndrome, bacterial infections, hypersecretory states associated with systemic mastocytosis or basophilic leukaemia and hyperhystaminemia, comprising administering to a subject a compound of formula (I) or a salt thereof according to claim 1.

9. A method of treatment of Alzheimer's disease, comprising administering to a subject a compound of formula (I) or a salt thereof according to claim 1.

10. A method of treating disorders resulting from elevated levels of COX-2 selected from the group consisting of: angiogenesis, arthritis, asthma, bronchitis, menstrual cramps, tendinitis, bursitis, neoplasia, ophthalmic diseases, pulmonary inflammations, central nervous system disorders, allergic rhinitis, atherosclerosis, endothelial disorders, organs and tissues preservation, and inhibition or prevention of platelet aggregation, comprising administering to a subject a compound of formula (I) or a salt thereof according to claim 1.

11. A pharmaceutical composition comprising a pharmaceutically acceptable carrier and a pharmaceutically effective amount of a compound of general formula (I) or a salt thereof according to claim 1.

12. A composition according to claim 11 in a suitable form for the oral, parenteral, rectal, topic and transdermic administration, by inhalation spray or aerosol or iontophoresis devices.

13. A liquid or solid pharmaceutical composition for oral, parenteral, rectal, topic and transdermic administration or inhalation in the form of tablets, capsules and pills optionally with enteric coating, powders, granules, gels, emulsions, solutions, suspensions, syrups, elixir, injectable forms, suppositories, in transdermal patches or liposomes, containing a compound of formula (I) according to claim 1 or a salt thereof and a pharmaceutically acceptable carrier.

* * * * *